United States Patent
Grubbs et al.

(10) Patent No.: US 6,794,534 B2
(45) Date of Patent: Sep. 21, 2004

(54) SYNTHESIS OF FUNCTIONALIZED AND UNFUNCTIONALIZED OLEFINS VIA CROSS AND RING-CLOSING METATHESIS

(75) Inventors: Robert H. Grubbs, Pasadena, CA (US); Arnab K. Chatterjee, Pasadena, CA (US); John P. Morgan, Pasadena, CA (US); Matthias Scholl, Cambridge, MA (US); Tae-Lim Choi, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/891,144

(22) Filed: Jun. 25, 2001

(65) Prior Publication Data

US 2002/0137978 A1 Sep. 26, 2002

Related U.S. Application Data

(60) Provisional application No. 60/213,757, filed on Jun. 23, 2000.

(51) Int. Cl.[7] .......................... C07C 69/52; C07C 57/02; C07C 233/00; C07C 6/00
(52) U.S. Cl. ....................... 560/205; 562/598; 564/161; 585/642
(58) Field of Search ................................ 560/205, 125; 562/598; 564/161, 159; 585/643, 364, 365, 366

(56) References Cited

U.S. PATENT DOCUMENTS

| | | | |
|---|---|---|---|
| 5,312,940 A | 5/1994 | Grubbs et al. | 556/136 |
| 5,342,909 A | 8/1994 | Grubbs et al. | 526/171 |
| 5,710,298 A | 1/1998 | Grubbs et al. | 556/22 |
| 5,728,785 A | 3/1998 | Grubbs et al. | 526/142 |
| 5,728,917 A | 3/1998 | Grubbs et al. | 585/653 |
| 5,750,815 A | 5/1998 | Grubbs et al. | 585/511 |
| 5,811,515 A | 9/1998 | Grubbs et al. | 530/330 |
| 5,831,108 A | 11/1998 | Grubbs et al. | 556/21 |
| 5,969,170 A | 10/1999 | Grubbs et al. | 556/21 |

FOREIGN PATENT DOCUMENTS

| | | | |
|---|---|---|---|
| CA | 2249019 | * 4/1999 | |
| DE | 19815275 | 10/1999 | C07F/15/00 |

OTHER PUBLICATIONS

Crowe et al, Journal of the American Chemical Society, Acrylonitrile Cross–Metathesis: Coaxing Olefin Metathesis Reactivity from a Reluctant Substrate, 1995, 117, pp. 5162–5163.*

Fürstner et al, Journal of Organic Chemistry, Ruthenium Carbene Complexes with N,N–Bis(mesityl)imidazol–2–ylidene Ligands: RCM Catalysts of Extended Scope, 2000, 65, pp. 2204–2207.*

Hermann, et al. "Chapter 3 Complexes of N–Heterocyclic Carbenes" Anorganisch–chemisches Institut der Technishen Universitat Munchen, Germany, pp. 85–112.

Weskamp, T. et al., "N–Heterocyclic Carbenes: Novel Ruthenium–Alkylidene Complexes," Journal of Organometallic Chemistry 582 (1999) pp. 362–365 [Received Mar. 1, 1999].

* cited by examiner

*Primary Examiner*—Johann Richter
*Assistant Examiner*—Paul A. Zucker
(74) *Attorney, Agent, or Firm*—Reed & Eberle LLP

(57) ABSTRACT

The invention is directed to the cross-metathesis and ring-closing metathesis reactions between geminal disubstituted olefins and terminal olefins, wherein the reaction employs a Ruthenium or Osmium metal carbene complex. Specifically, the invention relates to the synthesis of α-functionalized or unfunctionalized olefins via intermolecular cross-metathesis and intramolecular ring-closing metathesis using a ruthenium alkylidene complex. The catalysts preferably used in the invention are of the general formula

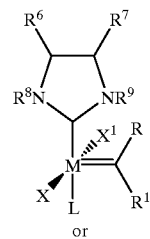

or

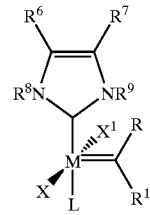

wherein:

M is ruthenium or osmium;

X and $X^1$ are each independently an anionic ligand;

L is a neutral electron donor ligand; and,

R, $R^1$, $R^6$, $R^7$, $R^8$, and $R^9$ are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl.

44 Claims, No Drawings

SYNTHESIS OF FUNCTIONALIZED AND UNFUNCTIONALIZED OLEFINS VIA CROSS AND RING-CLOSING METATHESIS

This application claims the benefit of U.S. Provisional Application Ser. No. 60/213,757, filed Jun. 23, 2000, the contents of which are incorporated herein by reference.

The U.S. Government has certain rights in this invention pursuant to Grant No. GM 31332 awarded by the National Institute of Health.

BACKGROUND

Metathesis catalysts have been previously described by for example, U.S. Pat. Nos. 5,312,940, 5,342,909, 5,728,917, 5,750,815, 5,710,298, and 5,831,108 and PCT Publications WO 97/20865 and WO 97/29135 which are all incorporated herein by reference. These publications describe well-defined single component ruthenium or osmium catalysts that possess several advantageous properties. For example, these catalysts are tolerant to a variety of functional groups and generally are more active than previously known metathesis catalysts. In an unexpected and surprising result, the inclusion of an imidazolidine ligand in these metal-carbene complexes has been found to dramatically improve the already advantageous properties of these catalysts. For example, the imidazolidine-based catalysts exhibit increased activity and selectivity not only in ring closing metathesis ("RCM") reactions, but also in other metathesis reactions including cross metathesis ("CM") reactions, reactions of acyclic olefins, and ring opening metathesis polymerization ("ROMP") reactions.

Trisubstituted carbon—carbon double bonds are a recurring motif in a diverse array of organic molecules. In particular, the generation of olefins with electron-withdrawing functionality, such as α-β unsaturated aldehydes, ketones, and esters, remains a difficult reaction in organic chemistry. Therefore, new stereoselective methods for generating functionalized trisubstituted olefins remain an ongoing challenge in the area of synthetic organic chemistry. A wide variety of methods have been investigated to date including intramolecular Claisen rearrangments, Wittig olefination, Julia couplings, Peterson olefinations, alkylation of sulfonyl hydrazones, and direct methods for the preparation of fluorinated trisubstituted alkenes. Transition metal mediated routes including hydromagnesization, hydrozirconation, and the use of organocuprates have also been reported, but often suffer from use of harsh stoichiometric reagents.

The olefin metathesis reaction has recently gained prominence in synthetic organic chemistry with the commercial availability of well-defined transition metal

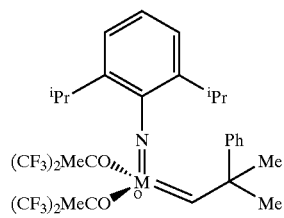

1

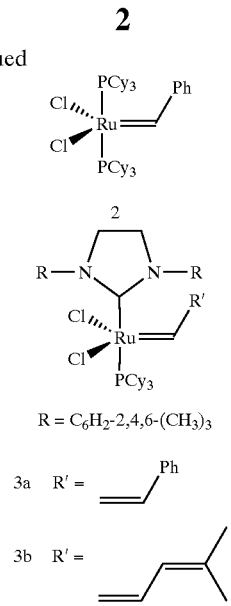

$R = C_6H_2\text{-}2,4,6\text{-}(CH_3)_3$

3a  R' = ⸺Ph

3b  R' = ⸺⟨ catalysts, such as the molybdenum alkoxy-imido alkylidene 1 and ruthenium benzylidene 2. In particular, ring-closing olefin metathesis (RCM) reactions have been widely utilized in the construction of a diverse variety of organic molecules. Approaches to generate olefins with vinylic functionality through the use of olefin cross-metathesis have been met with limited success. The intermolecular variant of olefin metathesis, terminal olefin cross-metathesis, has received less attention in the literature due to issues of product and olefin stereoisomer selectivity. However, renewed interest in this area has led to the recent development of new methodology for the selective cross-metathesis of terminal olefins using both 1 and 2. One of these initial reports, by Crowe and Goldberg, reported that acrylonitrile participated in a cross-metathesis reaction with a variety of terminal olefins. In an attempt to extend cross-metathesis beyond α-olefins, however, Crowe et al, reported that disubstituted olefins were unreactive cross-metathesis partners with styrene using 1. Moreover, other α,β-unsaturated carbonyl olefins, such enones and enoic esters, were not compatible with alkylidene 1 and therefore the methodology lacked generality. Recently, the highly active ruthenium-based olefin metathesis catalyst 3a,b containing a 1,3-dimesityl-4,5-dihydro-imidazol-2-ylidene ligand was found to efficiently catalyze the ring-closing metathesis (RCM) of a variety of acyclic dienes while exhibiting excellent functional group tolerance. Because ruthenium alkylidene 3a,b displayed unique activity towards previously metathesis inactive substrates using benzylidene 2, this prompted the investigation of metathesis of α-functionalized olefins. The homologation of terminal olefins with a variety of functional groups in a stereoselective manner would be a synthetically valuable transformation. In particular, the formation of tri-substituted olefins in a stereoselective manner would be highly valuable for production of pharmaceuticals, natural products, and functionalized polymers.

SUMMARY

The invention generally relates to the cross-metathesis and ring-closing metathesis reactions between geminal disubstituted olefins and terminal olefins, wherein the reaction employs a Ruthenium or Osmium metal carbene complex. Specifically, the invention relates to the synthesis of α-functionalized or unfunctionalized olefins via intermolecular cross-metathesis and intramolecular ring-closing metathesis using a ruthenium alkylidene complex. By α-functionalized olefins, it is meant that the olefin is substituted at the allylic position. Functional groups include, for example, carbonyls, epoxides, siloxanes, or perfluorinated alkenes and represent functional groups that make the olefin electron deficient by resonance or inductive effects. These functionalized olefins can be substituted or unsubstituted. Such substituents may be selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Further, the functional group or substituent can be selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen. The catalysts preferably used in the invention are of the general formula

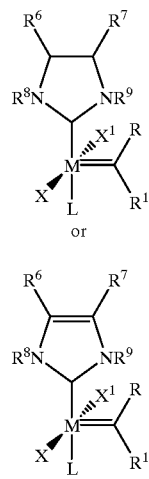

wherein:

M is ruthenium or osmium;

X and $X^1$ are each independently an anionic ligand;

L is a neutral electron donor ligand; and,

R, $R^1 R^6$, $R^7$, $R^8$, and $R^9$ are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Optionally, each of the R, $R^1 R^6$, $R^7$, $R^8$, and $R^9$ substituent group may be substituted with one or more moieties selected from the group consisting of $C_1$–$C_{10}$ alkyl, $C_1$–$C_{10}$ alkoxy, and aryl which in turn may each be further substituted with one or more groups selected from a halogen, a $C_1$–$C_5$ alkyl, $C_1$–$C_5$ alkoxy, and phenyl. Moreover, any of the catalyst ligands may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen. The inclusion of an imidazolidine ligand to the previously described ruthenium or osmium catalysts has been found to dramatically improve the properties of these complexes. Imidazolidine ligands are also referred to as 4,5-dihydro-imidazole-2-ylidene ligands. Because the imidazolidine-based complexes are extremely active, the amount of catalysts that is required is significantly reduced. The inventive method allows for an efficient one-step formation of functionalized trisubstituted olefins under mild reaction conditions and further demonstrates the utility of olefin metathesis in organic synthesis.

DETAILED DESCRIPTION OF THE PREFERRED EMBODIMENTS

The invention generally relates to cross-metathesis and ring-closing metathesis reactions between geminal disubstituted olefins and terminal olefins employing ruthenium alkylidenes. More particularly, the invention relates to the synthesis of unfunctionalized or functionalized trisubstituted and vicinally disubstituted olefins via intermolecular cross-metathesis and intramolecular ring-closing metathesis using imidazolidine based ruthenium and osmium carbene catalysts. The terms "catalyst" and "complex" herein are used interchangeably.

Unmodified ruthenium and osmium carbene complexes have been described in U.S. Pat. Nos. 5,312,940, 5,342,909, 5,728,917, 5,750,815, and 5,710,298, U.S. Application Ser. Nos. 09/539,840 and 09/576,370, and PCT Publication Nos. WO 00/58322 and WO 00/15339, the contents of all of which are incorporated herein by reference. The ruthenium and osmium carbene complexes disclosed in these patents all possess metal centers that are formally in the +2 oxidation state, have an electron count of 16, and are penta-coordinated. These catalysts are of the general formula

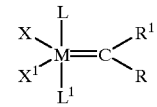

wherein:

M is ruthenium or osmium;

X and $X^1$ are each independently any anionic ligand;

L and $L^1$ are each independently any neutral electron donor ligand;

R and $R^1$ are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Optionally, each of the R or $R^1$ substituent group may be substituted with one or more moieties selected from the group consisting of $C_1$–$C_{10}$ alkyl, $C_1$–$C_{10}$ alkoxy, and aryl which in turn may each be further substituted with one or more groups selected from a halogen, a $C_1$–$C_5$ alkyl, $C_1$–$C_5$ alkoxy, and phenyl. Moreover, any of the catalyst ligands may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

The preferred catalysts used in the invention are as described above except that $L^1$ is an unsubstituted or substituted N-heterocyclic carbene. Preferably the N-heterocyclic carbene is of the formula:

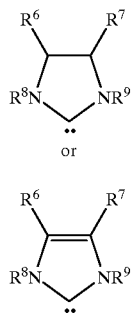

resulting in a complex of the general formula

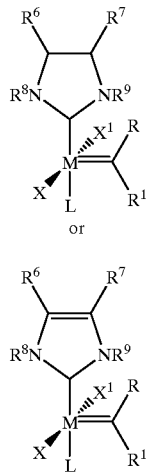

wherein:

$R^6$, $R^7$, $R^8$, and $R^9$ are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Imidazolidine ligands are also referred to as 4,5-dihydro-imidazole-2-ylidene ligands.

In preferred embodiments of the catalysts, the R substituent is hydrogen and the $R^1$ substituent is selected from the group consisting of $C_1$–$C_{20}$ alkyl, $C_2$–$C_{20}$ alkenyl, and aryl. In even more preferred embodiments, the $R^1$ substituent is phenyl or vinyl, optionally substituted with one or more moieties selected from the group consisting of $C_1$–$C_5$ alkyl, $C_1$–$C_5$ alkoxy, phenyl, and a functional group. In especially preferred embodiments, $R^1$ is phenyl or vinyl substituted with one or more moieties selected from the group consisting of chloride, bromide, iodide, fluoride, —$NO_2$, —$NMe_2$, methyl, methoxy and phenyl. In the most preferred embodiments, the $R^1$ substituent is phenyl or —C=C(CH$_3$)$_2$.

In preferred embodiments of the catalysts, L is selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether. In more preferred embodiments, L is a phosphine of the formula $PR^3R^4R^5$, where $R^3$, $R^4$, and $R^5$ are each independently aryl or $C_1$–$C_{10}$ alkyl, particularly primary alkyl, secondary alkyl or cycloalkyl. In the most preferred embodiments, L is each selected from the group consisting of -P(cyclohexyl)$_3$, -P(cyclopentyl)$_3$, -P(isopropyl)$_3$, and -P(phenyl)$_3$. L can also be an N-heterocyclic carbene. For example, L can be a ligand of the general formula:

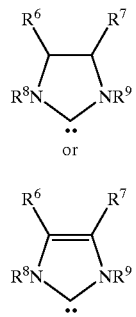

wherein $R^6$, $R^7$, $R^8$ and $R^9$ are as previously defined.

In preferred embodiments of the catalysts, X and $X^1$ are each independently hydrogen, halide, or one of the following groups: $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthio, $C_1$–$C_{20}$ alkylsulfonyl, or $C_1$–$C_{20}$ alkylsulfinyl. Optionally, X and $X^1$ may be substituted with one or more moieties selected from the group consisting of $C_1$–$C_{10}$ alkyl, $C_1$–$C_{10}$ alkoxy, and aryl which in turn may each be further substituted with one or more groups selected from halogen, $C_1$–$C_5$ alkyl, $C_1$–$C_5$ alkoxy, and phenyl. In more preferred embodiments, X and $X^1$ are halide, benzoate, $C_1$–$C_5$ carboxylate, $C_1$–$C_5$ alkyl, phenoxy, $C_1$–$C_5$ alkoxy, $C_1$–$C_5$ alkylthio, aryl, and $C_1$–$C_5$ alkyl sulfonate. In even more preferred embodiments, X and $X^1$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate. In the most preferred embodiments, X and $X^1$ are each chloride.

In preferred embodiments of the catalysts, $R^6$ and $R^7$ are each independently hydrogen, phenyl, or together form a cycloalkyl or an aryl optionally substituted with one or more moieties selected from the group consisting of $C_1$–$C_{10}$ alkyl, $C_1$–$C_{10}$ alkoxy, aryl, and a functional group selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen; and $R^8$ and $R^9$ are each is independently $C_1$–$C_{10}$ alkyl or aryl optionally substituted with $C_1$–$C_5$ alkyl, $C_1$–$C_5$ alkoxy, aryl, and a functional group selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

In more preferred embodiments, $R^6$ and $R^7$ are both hydrogen or phenyl, or $R^6$ and $R^7$ together form a cycloalkyl group; and $R^8$ and $R^9$ are each either substituted or unsubstituted aryl. Without being bound by theory, it is believed that bulkier $R^8$ and $R^9$ groups result in catalysts with improved characteristics such as thermal stability. In especially preferred embodiments, $R^8$ and $R^9$ are the same and each is independently of the formula

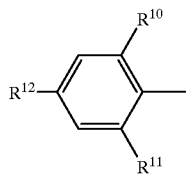

wherein:

R[10], R[11], and R[12] are each independently hydrogen, $C_1$–$C_{10}$ alkyl, $C_1$–$C_{10}$ alkoxy, aryl, or a functional group selected from hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen. In especially preferred embodiments, R[10], R[11], and R[12] are each independently selected from the group consisting of hydrogen, methyl, ethyl, propyl, isopropyl, hydroxyl, and halogen. In the most preferred embodiments, R[10], R[11], and R[12] are the same and are each methyl.

The invention discloses a novel method for the preparation of trisubstituted alkenes via intermolecular olefin cross-metathesis or intramolecular ring-closing metathesis of geminal disubstituted olefins and terminal olefins as shown in Scheme 1:

Scheme 1

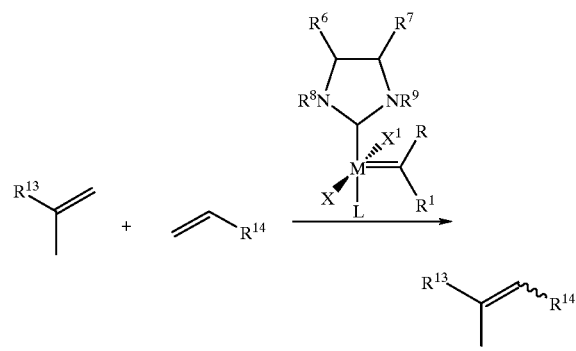

wherein X, X[1], L, R, R[1], R[6], R[7], R[8] and R[9] are as previously defined. As stated above, the use of an unsaturated N-heterocyclic carbene complex, for example one of the general formula:

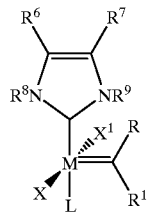

wherein X, X[1], L, R, R[1], R[6], R[7], R[8] and R[9] are as previously defined, may also be used. Preferably, the complex used is 1,3-dimesityl-4,5-dihydro-imidazol-2-ylidene ruthenium alkylidene complexes.

R[13] and R[14] are each independently a moiety selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_2$0 alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Optionally, each of the R[13] and R[14] substituent group may be substituted with one or more moieties selected from the group consisting of $C_1$–$C_{10}$ alkyl, $C_1$–$C_{10}$ alkoxy and aryl, that in turn may each be further substituted with one or more groups selected from a halogen, a $C_1$–$C_5$ alkyl, $C_1$–$C_5$ alkoxy, and phenyl. Moreover, R[13] and R[14] may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen. Further, R[13] and R[14] may be a substituted or unsubstituted functional group selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

The reaction in Scheme 1 results in good yields with moderate E selectivity. In addition, protected alcohols near the geminal disubstituted olefin improves reactivity for cross-metathesis.

Table 1 shows the results of studies of the use of 2-methyl-1-undecene as a unfunctionalized geminal disubstituted olefin for cross-metathesis (Table 1, Entries 1–4). Substrate 4 proved to be a reactive substrate for cross-metathesis, coupling vinyldioxolane, allyl sulfone, and 1,4-diacetoxy-cis-2,3-butene in good yields with moderate trans stereoselectivity. Particularly notable, allyl sulfone is a very reactive substrate for cross-metathesis (87% isolated yield, Table 1, Entry 2) using 3a,b, but yields no cross-metathesis product using 2.

TABLE 1

| Entry | Geminal Olefin Substrate | Terminal Olefin | Product | Yield | E/Z ratio |
|---|---|---|---|---|---|
| 1 | ![sub1] | ![term1] | ![prod1] | 67 | 3:1 |

TABLE 1-continued

| Entry | Geminal Olefin Substrate | Terminal Olefin | Product | Yield | E/Z ratio |
|---|---|---|---|---|---|
| 2 | | | | 87 | 3:4:1 |
| 3 | | | | 53 | 2 5 1 |
| 4 | | | | 60 | 2 3:1 |
| 5 | | | | 80 | 2 8:1 |
| 6 | | | | 81 | 4:1 |

Functionalized disubstituted olefins (Table 1, Entries 5 and 6) also proved excellent substrates for this reaction, and showed improved yields relative to 2-Methyl-1-undecene. Without being bound by theory, the benzoate ester functionality may increase reactivity of the geminal olefins with the catalytic ruthenium species. In addition, maintaining a low concentration of terminal olefin homodimer also increases the cross-metathesis yields. In the reaction shown in Table 1, Entry 1, the vinyldioxolane component (3 equivalents) was added in four equal parts over a six-hour period. This maintained a low concentration of dioxolane homodimer and increased the isolated yield of cross-methathesis product by about 10 percent. It should also be noted that in all reactions, the disubstituted olefin does not undergo self-metathesis, enabling quantitative recovery of unreacted material. Protected allylic and homoallylic alcohols are also suitable under the reaction conditions.

Another aspect of the inventive method is the synthesis of functionalized olefins via intermolecular cross-metathesis and intramolecular ring-closing metathesis using a metal carbene metathesis catalyst.

In exploring a variety of geminally disubstituted olefins in cross-metathesis, it was noted that methyl methacrylate 4 participates in a novel and unexpected cross-metathesis reaction with terminal olefins 5–7 to generate the trisubstituted enoic ester in moderate yield with excellent stereoselectivity (Scheme 2):

Scheme 2

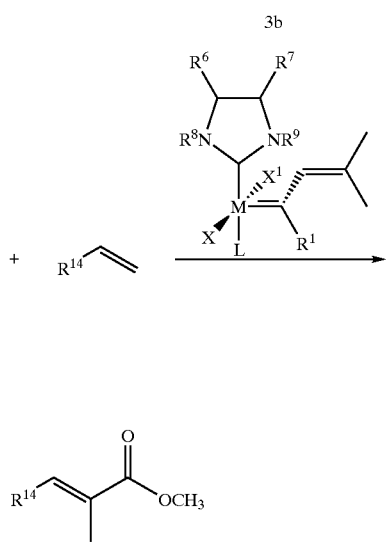

wherein M, L, X, $X^1$, $R^1$, $R^6$, $R^7$, $R^8$, $R^9$ and $R^{14}$ are as previously defined. Preferably, and as seen in Scheme 2, $R^1$ is a vinylidene. However, any of the previously described metathesis catalysts can also be used in the reaction.

The results of the cross-metathesis of a variety of α-carbonyl containing compounds can be seen in Table 2.

TABLE 2

| entry | terminal olefin | α-functionalized olefin (equiv.) | product | isolated yield(%) | E/Z |
|---|---|---|---|---|---|
| 1 | 5 | CH$_2$=C(CH$_3$)CO$_2$CH$_3$ (2.0) | TBSO-(CH$_2$)$_7$-CH=C(CH$_3$)CO$_2$CH$_3$ | 75 | >20:1 |
| 2 | 6 | CH$_2$=CHCO$_2$CH$_3$ (2.0) | BzO-(CH$_2$)$_7$-CH=CH-CO$_2$CH$_3$ | 91 | >20:1 |
| 3 | 7 | CH$_2$=C(CH$_3$)CHO (2.0) | AcO-(CH$_2$)$_3$-CH=C(CH$_3$)CHO | 92 | >20:1 |
| 4 | 7 | CH$_2$=CHCHO (2.0) | AcO-(CH$_2$)$_3$-CH=CH-CHO | 62 | >20:1 |
| 5 | 7 | CH$_3$CH=CHCHO (2.0) | AcO-(CH$_2$)$_3$-CH=CH-CHO | 92 | >20:1 |
| 6 | 7 | CH$_2$=CHC(O)Ph (2.0) | AcO-(CH$_2$)$_3$-CH=CH-C(O)Ph | 99 | >20:1 |
| 7 | 7 | CH$_2$=C(CH$_3$)C(O)CH$_3$ (2.0) | AcO-(CH$_2$)$_3$-CH=C(CH$_3$)C(O)CH$_3$ | 95 | >20:1 |

Particularly notable are the excellent yields attained with ketones and aldehydes (Table 2, Entry 3–7). In addition, the stereoselectivities of these reactions are excellent, making them synthetically practical for di- and trisubstituted olefins. Particularly notable is the excellent yield attained with esters and aldehydes (Table 2, Entry 1–3). In a related result, CM of acrylic acid with terminal olefin 7 gave a quantitative yield of the cross product. This route provides a mild and efficient method for the synthesis of a variety of acrylic acids that avoids harsh reaction conditions such as oxidation of alcohols to acids and avoids the use of protecting groups on the acid moiety. In addition, in the optimization of reaction conditions, lowering reaction temperatures to about 23 to about 25° C. and reactions with no excess of one olefin partner, have also been led to successful CM. The unexpected result was that the reactions conducted at room temperature not only afford a cross product in substantial yield but also do not require an excess of one olefin partner. In the case of terminal aldehyde CM a particularly interesting and unexpected result was obtained. Due to impurities in commercially available acrolein, trans-crotonaldehyde was also investigated as an aldehyde source in CM. As demonstrated in Table 1, Entries 4 and 5, the use of crotonaldehyde is a significantly higher yielding reaction. A visible difference in the two reactions is the loss of gaseous side products ethylene (Entry 4) vs. propylene (Entry 5). Without being bound by theory, it is proposed that the use of crotonates instead of acrylates also increase CM yields due to the catalytic intermediates involved under analogous reaction conditions.

Another inventive aspect of the invention involves the cross-metathesis of acrylamides. Table 3 lists the results of the cross-metathesis of example acrylamides and terminal olefins using complex 3a:

TABLE 3

| entry | acrylamide | Terminal olefin | mol % 3a | Product | Isolated Yield of CM (E/Z) |
|---|---|---|---|---|---|
| 1a | Me$_2$N-C(O)-CH=CH$_2$ | 5 | 5 mol % | Me$_2$N-C(O)-CH=CH-(CH$_2$)$_7$-OTBS | 39% (25:1) |
| 1b | Me$_2$N-C(O)-CH=CH$_2$ | 5 | 10 mol % | Me$_2$N-C(O)-CH=CH-(CH$_2$)$_7$-OTBS | 83% (25:1) |
| 2 | Cy$_2$N-C(O)-CH=CH$_2$ | 5 | 5 mol % | Cy$_2$N-C(O)-CH=CH-(CH$_2$)$_7$-OTBS | 77% (>20:1) |

TABLE 3-continued

| entry | acrylamide | Terminal olefin | mol % 3a | Product | Isolated Yield of CM (E/Z) |
|---|---|---|---|---|---|
| 3 | iPr-NH-C(O)-CH=CH2 | 8 | 5 mol % | iPr-NH-C(O)-CH=CH-(CH2)3-OTHP | 80% (>20:1) |
| 4 | MeO-N(Me)-C(O)-CH=CH2 | 8 | 5 mol % | MeO-N(Me)-C(O)-CH=CH-(CH2)3-OTHP | 89% (60:1) |
| 5 | H2N-C(O)-CH=CH2 | 5 | 5 mol % | H2N-C(O)-CH=CH-(CH2)7-OTBS | 89% (>20:1) |
| 6 | Ph-NH-C(O)-CH=CH2 | 8 | 5 mol % | Ph-NH-C(O)-CH=CH-(CH2)3-OTHP | 90% (>20:1) |
| 7 | Ph-N(Me)-C(O)-CH=CH2 | 8 | 5 mol % | Ph-N(Me)-C(O)-CH=CH-(CH2)3-OTHP | 97% (28:1) |
| 8 | Ph2N-C(O)-CH=CH2 | 8 | 5 mol % | Ph2N-C(O)-CH=CH-(CH2)3-OTHP | 100% (40:1) |
| 9 | oxazolidinone-C(O)-CH=CH2 | 8 | 5 mol % | oxazolidinone-C(O)-CH=CH-(CH2)3-OTHP | 87% (60:1) |

Initially, dimethyl acrylamide (entry 1a) was tried and a disappointingly low yield of about 39% of CM product was obtained. However, upon using higher catalyst loading, (10 mol % of catalyst 1) and about 1.5 equivalents of terminal olefin, the yield was improved to about 83% (entry 1b). Other substrates show good to excellent yields ranging from about 77% to about 100% with excellent diastereoselectivity (>25:1 trans:cis).

Particularly valuable is the compatibility with Weinreb amide (entry 4) and oxazolidinone imides (entry 9). These functional groups are used widely in organic synthesis and CM provides synthons for further manipulations. In particular, oxazolidinone imides are widely used in asymmetric reactions such as Michael additions, aldol, and Diels-Alder reactions. For representative examples of oxazolidinone chemistry see (a) D. A. Evans, M. C. Willis, J. N. Johnston, Org. Lett. 1999, 1, 865. (b) D. A. Evans, J. Bartroli, T. L. Shih, J. Am. Chem. Soc. 1981, 103, 2127; b) D. A. Evans, M. D. Ennis, D. J. Mathre, J. Am. Chem. Soc. 1982, 104, 1737. (c) D. A. Evans, S. J. Miller, T. Lectka, P. von Matt, J. Am. Chem. Soc. 1999, 121, 7559; the contents of all of which are incorporated herein by reference. There is an effect of the acrylamide substituents on the CM efficiency. Electron-donating substituents, such as alkyl groups, increase the nucleophilicity of the carbonyl oxygen and lower CM yields result. Without being bound by theory, this may be attributed to a chelation effect on the Ru metal center and thereby lowers the overall CM reaction rate. Interestingly, where electronic contributions are similar, the chelation effect can be decreased by bulky substituents on the amide nitrogen making the carbonyl oxygen less sterically accessible (Table 3, Entry 1a versus Entry 2). Other functional groups at the vinylic position were also investigated in cross-metathesis, and the results are summarized in Table 4.

TABLE 4

| entry | terminal olefin | α-functionalized olefin (equiv.) | | product | | % isolated yield | E/Z |
|---|---|---|---|---|---|---|---|
| 1 | 5 | 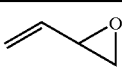 19 | (2.0) |  22 | | 38 | 5:1 |
| 2 | 5 | 19 | (4.0)[c] | 22 | | 55 | 5:1 |
| 3 | 6 | 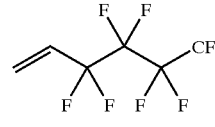 20 | (2.0) | 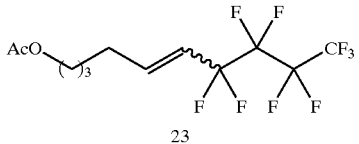 23 | | 75 | 2.3:1 |
| 4 | 6 | 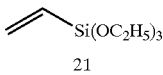 21 | (2.0) |  24 | | 90 | 11:1 |

Vinyl epoxides, such as butadiene monoxide 19 and electron-deficient perfluorinated alkenes 20 participate in cross-metathesis in moderate yields (Table 4, Entry 1–3) and represent other α-functionalized olefins that participate in CM. The addition of four equivalents of epoxide 19 increased the yield of cross-product 22 (Table 4, Entry 2) and may be correlated to the volatility of butadiene monoxide. Vinyl siloxanes are also very good cross-metathesis partners using 3a,b (Table 4, Entry 4), but yielded only about 36% of cross-product 24 with ruthenium benzylidene 2. These siloxanes provide useful synthons for further coupling reactions such as Suzuki-type aryl halide cross-couplings.

Finally, ring closing metathesis (RCM) reactions of substrates bearing vinyl functional groups are summarized in Table 5:

TABLE 5

| entry | α-functionalized diene | product | yield (%)[b] |
|---|---|---|---|
| 1 | 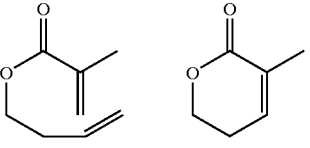 | 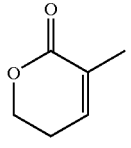 | 86 |
| 2 | 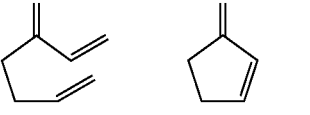 | 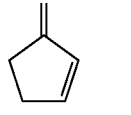 | 93 |
| 3 | 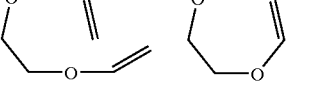 | 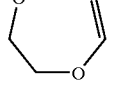 | 93 |
| 4 | 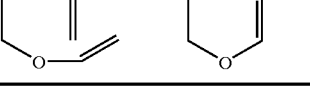 | 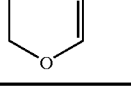 | 0 |

Six and five membered α-β unsaturated enones (Table 5, Entry 1-2) were formed in excellent yields, including the trisubstituted lactone (Table 5, Entry 1). Also, the unprecedented ring-closing reaction of vinyl ether proceeds in good conversion to give cyclic product (Table 5, Entry 3). Without being bound by theory, the allylic ether may be initially reacting with the catalyst followed by a fast reaction with the vinyl ether. This would minimize the formation of a stabilized Fischer-type carbene with the catalyst and allow for catalytic turnover. This is further evidenced by the inability to ring close substrates where both alkenes are vinyl ethers using catalyst 3b. In addition, larger ring structures containing α-functionalized groups can also be synthesized using the inventive method. Such α-functionalized groups include, for example, epoxides, perfluorinated olefins, and siloxanes.

Another inventive aspect of the invention is the process in which an electron deficient olefin is reacted with an aliphatic olefin or where two different sets of electron-deficient olefins are reacted with each other. In particular, the invention provides a process for preparing di- or tri-substituted olefins comprising contacting a substituted or unsubstituted aliphatic olefin with a substituted or unsubstituted electron-deficient olefin in the presence of a metal carbene metathesis catalyst. Substituted aliphatic olefins include any mono-, di-, or trisubstituted olefin wherein the olefin contains an alkyl group. Examples of this process can also be seen in Table 2 where the aliphatic olefin is the terminal olefin. However, the substituted olefin may also be prepared when the aliphatic olefins is an internal olefins. The invention also provides a process for preparing di- or tri-substituted olefins comprising contacting a substituted or unsubstituted electron deficient olefin with another substituted or unsubstituted electron deficient olefin in the presence of a metal carbene metathesis catalyst. The first and second electron-deficient olefins may be the same or different. Preferably one olefin is a substituted or unsubstituted styrene and the other olefin contains an α-carbonyl group, for example, an acrylate or acrylamide. Alternatively, both olefins may contain α-carbonyl group. Either or both of these electron-deficient olefins may be substituted or unsubstituted. Substituents on the electron-deficient olefins and the aliphatic olefins may include one or more groups selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Optionally, the substituent group may be substituted with one or more moieties selected from the group consisting of $C_1$–$C_{10}$ alkyl, $C_1$–$C_{10}$ alkoxy, and aryl, which in turn may each be further substituted with one or more groups selected from a halogen, a $C_1$–$C_5$ alkyl, $C_1$–$C_5$ alkoxy, and phenyl. Moreover, the olefins may include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

Styrenes are one class of electron-deficient olefins that have been examined previously in olefin cross-metathesis with early heterogeneous systems and molybdenum-based systems. In both of these cases terminal olefins were used as the other olefin partner. In addition to examples using simple terminal olefins, it has been demonstrated that styrenes react with acrylamides in high yields with catalyst 1. The yields with styrene show a similar trend in yield (ranging from about 25% to about 87%) when comparing nitrogen substituents using catalyst 3a (Table 6).

TABLE 6

| entry | acrylamide | mol% 3a | Product | Isolated Yield of CM |
|---|---|---|---|---|
| 1a | (N,N-dimethyl acrylamide) | 5 mol % | (N,N-dimethyl cinnamamide) | 25% |
| 1b | | 10 mol % | | 57% |
| 2 | Cy$_2$N-acrylamide | 5 mol % | Cy$_2$N-cinnamamide | 62% |
| 3 | isopropyl acrylamide | 5 mol % | isopropyl cinnamamide | 66% |
| 4 | N-methoxy-N-methyl acrylamide | 5 mol % | N-methoxy-N-methyl cinnamamide | 69% |
| 5 | H$_2$N-acrylamide | 5 mol % | H$_2$N-cinnamamide | 69% |
| 6 | N-phenyl acrylamide | 5 mol % | N-phenyl cinnamamide | 83% |
| 7 | N-methyl-N-phenyl acrylamide | 5 mol % | N-methyl-N-phenyl cinnamamide | 87% |

TABLE 6-continued

| entry | acrylamide | mol% 3a | Product | Isolated Yield of CM |
|---|---|---|---|---|
| 8 | Ph₂N-C(=O)-CH=CH₂ | 5 mol % | Ph₂N-C(=O)-CH=CH-Ph | 40% |
| 9 | oxazolidinone-N-C(=O)-CH=CH₂ | 5 mol % | oxazolidinone-N-C(=O)-CH=CH-Ph | 63% |

This reaction is valuable in that it offers the possibility of a variety of cinnamides by cross-metathesis (CM).

Yet another inventive aspect of the invention is the use of styrenes as CM partners, in particular with catalysts 3a or 3b. Some previous art has demonstrated limited reactivity of styrenes in CM using 2 such as trialkyloxysilanes. In addition, the reaction allyl glycosides with a variety of para-substituted styrenes have been investigated with 2. However, prior to the invention, an extended scope of styrenes has not been investigated with catalyst 3a,b or terminal olefins. A novel aspect of the invention is the reaction between an α-functionalized olefin with a substituted or unsubstituted styrene, wherein the substitution on the styrene occurs on the aromatic or olefinic carbons, or both. As styrenes are electron-deficient olefins, a substituted styrene can include any of the substituent groups listed above for the electron-deficient olefins. In particular, reactions with a variety of substituted styrene and acrylates yielding Heck-type reaction products were synthesized by olefin metathesis (Table 7).

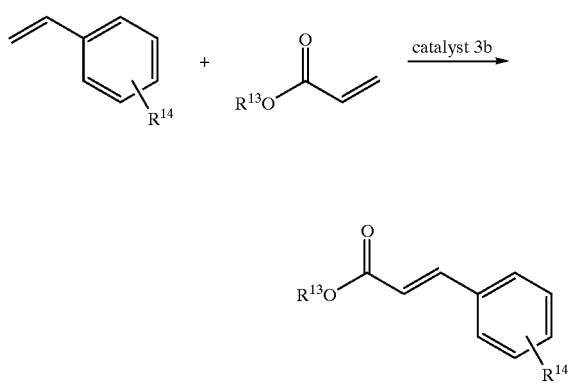

TABLE 7

| Entry | | Acrylate equiv. | Isolated Yield | E/Z Ratio |
|---|---|---|---|---|
| 1 | $R^{14}$ = H, $R^{13}$ = $CH_3$ | 2 | 92 | >20:1 |
| 2 | $R^{14}$ = 4-$CH_3$, $R^{13}$ = $CH_2CH_3$ | 2 | 99 | >20:1 |

TABLE 7-continued

| Entry | | Acrylate equiv. | Isolated Yield | E/Z Ratio |
|---|---|---|---|---|
| 3 | $R^{14}$ = 4-t-Bu, $R^{13}$ = $CH_2CH_3$ | 1.1 | 99 | >20:1 |
| 4 | $R^{14}$ = 2,4-Dimethyl, $R^{13}$ = $CH_2CH_3$ | 2 | 87 | >20:1 |
| 5 | $R^{14}$ = 4-Ph, $R^{13}$ = $CH_2CH_3$ | 2.2 | 90 | >20:1 |
| 6 | $R^{14}$ = 4-CHO, $R^{13}$ = $CH_2CH_3$ | 2 | 83 | >20:1 |
| 7 | $R^{14}$ = 4-Oac, $R^{13}$ = $CH_2CH_3$ | 1 | 88 | >20:1 |
| 8 | $R^{14}$ = 4-$NO_2$, $R^{13}$ = $CH_3$ | 2 | 89 | >20:1 |
| 9 | $R^{14}$ = 4-Cl, $R^{13}$ = $CH_3$ | 2 | 94 | >20:1 |
| 10 | $R^{14}$ = 4-Br, $R^{13}$ = $CH_2CH_3$ | 2 | 98 | >20:1 |
| 11 | $R^{14}$ = 2-F, $R^{13}$ = $CH_2CH_3$ | 2 | 72 | >20:1 |
| 12 | $R^{14}$ = 2-Cl, $R^{13}$ = $CH_2CH_3$ | 2 | 62 | >20:1 |
| 13 | $R^{14}$ = 2-Br, $R^{13}$ = $CH_2CH_3$ | 2 | 49 | >20:1 |

Of particular note is the use of ortho-substituents that are previously unprecedented (Table 7, Entries 4, 11–13). In addition, a variety of reactive functional groups such as nitro groups and benzaldehydes are amenable to the reaction conditions. Without being bound by theory, it is suspected that an even wider range of substituents can be used on the styrene segment of the coupling strategy. Two important additions to the reaction are the use of α,β-unsaturated ketones and aldehydes to styrenes. Further, yet another unexpected result of the invention is that the corresponding stilbene may also be used in the reactions and demonstrates the reversibility of the cross-metathesis reactions. For example, when using a substituted styrene with an α-functionalized olefin, the by-product, stilbene, can be reacted with α-functionalized olefins to form more cross-product (Table 8). This has been undiscovered in the styrene cross-metathesis literature with any homogeneous catalysts. In addition, without being bound by theory, it is proposed that the use of β-methylstyrene instead of acrylates will also increase CM yields due to the catalytic intermediates involved under analogous reaction conditions.

TABLE 8

| Stilbene | Functionalized olefin (equiv.) | Product | Isolated Yield | E/Z ratio |
|---|---|---|---|---|
| (Z)-stilbene | ethyl acrylate (2 eq.) | ethyl cinnamate | 88 | >20:1 |
| (E)-stilbene | ethyl acrylate (2 eq.) | ethyl cinnamate | 93 | >20:1 |
| bis(2,4-dimethylphenyl) stilbene | ethyl acrylate (2 eq.) | ethyl cinnamate | 70 | >20:1 |
| (E)-stilbene | cis-1,4-diacetoxy-2-butene (2 eq.) / (1 eq.) | cinnamyl acetate | 84 / 51 | >20:1 / >20:1 |
| (E)-stilbene | 4-nitrostyrene (0.5 eq.) | 4-nitrostilbene | 88 | >20:1 |

Further, it was determined that in the cross-metathesis with styrenes, rapid formation of stilbenes were followed by productive cross-metathesis. However, a new class of styrenes was found to form stilbenes slowly and allowed for the formation of selective cross-metathesis products with terminal olefins. Examples of these styrenes are listed in Table 9:

TABLE 9

| Styrene | Terminal olefin | Styrene : α-olefin | Product | Isolated CM Yield |
|---|---|---|---|---|
| styrene | THPO-(CH₂)₄-CH=CH₂ | 1 : 1 / 4 : 1 | THPO-(CH₂)₄-CH=CH-Ph | 47% / 70% |
| 2,4-dimethylstyrene | AcO-(CH₂)₄-CH=CH₂ | 3 : 1 | AcO-(CH₂)₄-CH=CH-(2,4-dimethylphenyl) | 73% |

TABLE 9-continued

| Styrene | Terminal olefin | Styrene · α-olefin Product | | Isolated CM Yield |
|---|---|---|---|---|
| 2-bromostyrene | AcO-(CH2)4-CH=CH2 | 1 1<br>3 1 | AcO-(CH2)4-CH=CH-(2-bromophenyl) | 80%<br>98% |
| styrene | CH2=CH-CH2-CH(OBz)-CH3 | 2 1 | CH3-CH(OBz)-CH2-CH=CH-phenyl | 81% |

A point to note is that ortho-substitutions in Table 9, Entries 2 and 3 represent selective CM reactions and that the homoallylic substitution in Entry 4 also directs selective CM.

In the previously mentioned reactions with α,β-unsaturated carbonyl containing compounds, mechanistic studies indicated that the reactions described in Table 2 and 3 are produced predominantly via a ruthenium carbene species of the terminal olefin component, followed by a quick reaction with an electron-deficient component, such as an acrylate. However, it was determined that, in fact, a variety of reactions could be performed where the resting ruthenium carbene state lies with electron-deficient component. This allows a much wider range of products available by cross-metathesis. Table 10 lists some example results:

TABLE 10

| Entry | Substrate | Product[a] | Isolated yield |
|---|---|---|---|
| 1 | n-butyl acrylate | di-n-butyl fumarate | 87% |
| 2 | cyclohexyl acrylate | dicyclohexyl fumarate | 75% |
| 3 | tert-butyl acrylate | di-tert-butyl fumarate | 94% |
| 4 | 1-adamantyl acrylate | di(1-adamantyl) fumarate | 80% |
| 5 | 1-octen-3-one (n-hexyl vinyl ketone) | bis(n-hexyl) enedione | 77% |

TABLE 10-continued

| Entry | Substrate | Product[a] | Isolated yield |
|---|---|---|---|
| 6 | cyclohexyl vinyl ketone | (E)-1,4-dicyclohexylbut-2-ene-1,4-dione | 95% |
| 7 | ethyl vinyl ketone | (E)-oct-4-ene-3,6-dione | 94% |

In addition to dimerizations, these reactions can also be applied to the reaction of acrylates with 1,1-seminally disubstituted as summarized in Table 11:

TABLE 11

| entry | Carbene Precusor | Cross-partner | Product | Isolated yield |
|---|---|---|---|---|
| 1 | methyl vinyl ketone | methyl acrylate | methyl (E)-4-oxopent-2-enoate | 41% |
| 2 | ethyl vinyl ketone | tert-butyl acrylate | tert-butyl (E)-4-oxohex-2-enoate | 41% |
| 3 | ethyl acrylate | 2-methylhept-1-ene | ethyl 3-methyloct-2-enoate | 83% |
| 4 | acrylic acid | 2-methylhept-1-ene | 3-methyloct-2-enoic acid | 83% |
| 5 | (E)-pent-3-en-2-one | 2-methylhept-1-ene | 3-methylundec-3-en-2-one | 68% |
| 6 | tert-butyl acrylate | methylenecyclohexane | tert-butyl 2-cyclohexylideneacetate | 75% |
| 7 | acrylic acid | methylenecyclohexane | 2-cyclohexylideneacetic acid | 83% |
| 8 | (E)-pent-3-en-2-one | methylenecyclohexane | 1-cyclohexylidenebutan-2-one | 99% |

Similar to the styrenes, the substitution can also occur on the olefinic carbons. The gem substitution can occur on the terminal or α-functionalized olefin.

Finally, a variety of reactions used allylic substituted terminal olefin with acrylates in cross-metathesis. For example the cross-metathesis of methyl acrylate and allyl alcohol proceeded in about 92% isolated yield with the reaction conditions listed in Table 2. In addition, a double CM reaction was accomplished with 1,5-hexadiene and four equivalents of acrylate in about 91% yield. Homoallylic substitution, such as ester groups and free hydroxyl groups, is also tolerable to the reaction conditions.

The following examples show the cross-metathesis and ring-closing metathesis of a variety of electron-deficient olefins employing ruthenium alkylidene 3a,b. These examples are merely illustrative and are not intended to limit the scope of the invention.

EXAMPLE 1
Representative Procedure of Preparation of Ruthenium Alkylidene 3a,b:

A 250-mL flame-dried round bottom flask equipped with a magnetic stirbar was charged with 1,3-dimesityl-4,5-dihydro-imidazolium tetrafluoroborate (3.08 g, 7.80 mmol, 1.6 equiv.) and dry THF (30 mL) under nitrogen atmosphere. A solution of potassium tertbutoxide (0.88 g, 7.80 mmol, 1.6 equiv.) in dry THF (30 mL) was slowly added at room temperature. The reaction mixture was allowed to stir for ½ hour and was then slowly transferred to a 500-mL flame-dried Schlenk flask containing a solution of $RuCl_2$ $(=CH=C(CH_3)_2)(PCp_3)_2$ (3.50 g, 4.88 mmol, 1.0 equiv.) in dry toluene (200 mL). This mixture was stirred at 80° C. for 15 min, at which point the reaction was complete as indicated by 'H NMR. The reaction mixture was filtered through a glass frit under argon and all volatiles were removed under high vacuum. The residue was recrystallized three times from anhydrous methanol (40 mL) at −78° C. to give 3 as a pinkish-brown microcrystalline solid (2.95 g) in 77% yield: 'H NMR (400 MHz, C6N, PPM) δ 19.16 (1H, d, J=11 Hz), 7.71 (1H, d, J=11 Hz), 6.89 (2H, s), 6.62 (2H, s), 3.36–3.24 (4H, m), 2.80 (6H, s), 2.54 (6H, s), 2.41–1.26 (27H, br m), 2.20 (3H, s), 2.02 (3H, s), 1.06 (3H, s), 0.90 (3H, s); 3'P NMR (161.9 MHz, CA, ppm) δ 28.05; HRMS (FAB) calcd for C4,H6,C12NZPRu [M+j 784.2993, found 784.2963.

EXAMPLE 2
Representative Procedures for the Formation of Trisubstituted Olefinic Products:

a) 2-methyl-1-undecene (110 μL, 0.5 mmol) and 5-hexenyl-1-acetate (170 μL, 1.0 mmol) were simultaneously added via syringe to a stirring solution of 3 (20 mg, 0.024 mmol, 4.8 mol %) in $CH_2Cl_2$ (2.5 mL). The flask was fitted with a condenser and refluxed under nitrogen for 12 hours. The reaction mixture was then reduced in volume to 0.5 ml and purified directly on a silica gel column (2×10 cm), eluting with 9:1 hexane:ethyl acetate. Clear oil was obtained (83 mg, 60% yield, 2.3:1 trans/cis as determined by relative intensity of alkene $^{13}C$ peaks at 125.0 and 124.2 ppm). $^1H$ NMR (300 MHz, $CDCl_3$, ppm): 5.08 (1H, t, J=2.0 Hz), 4.04 (2H, t, J=6.0 Hz), 2.03 (3H, obs s), 2.01–1.91 (2H, m), 1.69–1.59 (2H, m), 1.56 (3H, obs s), 1.47–1.05 (16H, broad m), 1.05–0.84 (3H, t, J=6.8 Hz) $^{13}C$ NMR (75 MHz, $CDCl_3$, ppm): 171.7, 136.7, 136.4, 150.0, 124.2, 123.3, 65.1, 40.3, 32.5, 32.3, 30.2, 29.9, 28.8, 28.6, 28.5, 28.0, 26.7, 23.2, 21.5, 16.4, 14.7. $R_f$=0.35

EXAMPLE 3
Representative Procedure of Preparation of Product in Table 2 Entry 1:

9-Decen-1(tert-butyldimethylsilane)-yl (165 μL, 0.51 mmol) and Methyl methacrylate (110 μl, 1.00 mmol) were added simultaneously via syringe to a stirring solution of 3 (21 mg, 0.026 mmol, 5.2 mol %) in $CH_2Cl_2$ (2.5 ml). The flask was fitted with a condenser and refluxed under nitrogen for 12 hours. The reaction mixture was then reduced in volume to 0.5 ml and purified directly on a silica gel column (2×10 cm), eluting with 9:1 hexane:ethyl acetate. Viscous oil was obtained (123 mg, 72% yield, trans/cis as determined by relative heights at 143.2 and 143.1 ppm of $^{13}C$ NMR spectra) and is representative of all the reactions in this table.
Reaction at room temperature:

For example, in the reaction in Table 2, Entry 2 the reaction is conducted as follows: To a solution of 3a in $CH_2Cl_2$ (0.2M) at 23–25° C. was added sequentially by syringe 5-Acetoxy-1-hexene (1 equiv) and methyl acrylate (1.05 equiv). The flask placed under a flow of nitrogen, and the reaction mixture was allowed to stir at the 23–23° C. temperature range and was maintained at that temperature for 12 h. The black reaction mixture was concentrated to 0.5 mL by rotary evaporation. The resulting residue was purified by silica gel chromatography (2×10 cm, 9:1 hexane:ethyl acetate), affording cross-product in 92% isolated yield.

EXAMPLE 4
Representative Procedure for Reactions in Table 3:

To a flask charged with amide (1.0 equiv) in $CH_2Cl_2$ (0.2M), catalyst 1 (0.05 equiv in $CH_2Cl_2$) was added by cannulation followed by addition of terminal olefin (1.25 equiv) via syringe. The flask was fitted with a condenser and refluxed under argon for 15 hours. TLC analysis was used to monitor the reactions. After the solvent was evaporated, the product was purified directly on a silica gel column to provide products as either viscous oils or white solids. A slight modification was made for the reaction on Table 3, Entry 1b where 1.5 equivalents of terminal olefin were used and a higher catalyst loading was used (10 mol %). These conditions increase the CM yields for all of the reactions described Table 3.

EXAMPLE 5
Representative Procedure of Preparation of Product in Table 4, Entry 1:

The reaction was conducted by analogy to the reactions mentioned above: 9-Decen-1-yl benzoate (145 μl, 0.52 mmol) and butadiene monoxide (160 μl, 1.98 mmol) and were added simultaneously via syringe to a stirring solution of 3a,b (21 mg, 0.027 mmol, 5.0 mol %) in $CH_2Cl_2$ (2.5 ml). The flask was fitted with a condenser and refluxed under nitrogen for 12 hours. The reaction mixture was then reduced in volume to 0.5 ml and purified directly on a silica gel column (2×10 cm), eluting with 20:1 hexane:ethyl acetate. Clear oil was obtained (95 mg, 55% yield, 5:1 trans/cis as determined by relative integrations of $^1H$ peaks at 5.94 and 5.75 ppm). The only difference in experimental procedure is in Entry 2 where two additional equivalents (4 equivalents total) of butadiene monoxide are added via a syringe pump over 12 hours. All of the reaction yields can be optimized with this change in the procedure.

EXAMPLE 6
Representative Procedure of Preparation of Product in Table 5, Entry 3:

A 250 mL oven-dried round bottom flask equipped with a stir bar was charged with $CH_2Cl_2$ (156 mL), mixed ether diene (1.00 g, 7.80 mmol, 1 equiv.) and catalyst 3b (331 mg, 0.42 mmol, 0.05 equiv.). The reaction mixture was refluxed overnight at which time the $^1H$ NMR indicated complete disappearance of the starting material. $CH_2Cl_2$ was distilled off at ambient pressure and the product was purified by bulb-to-bulb distillation to yield the product as colorless oil (382 mg, 3.78 mmol, 49% yield). The only difference for the reactions in Table 4 entries 1 and 2 are that reaction purification is by column chromatography in 10:1 hexanes:ethyl acetate eluant. Evaporation of solvent yielded products as clear oils.

EXAMPLE 7
Representative Procedure for Reactions in Table 6:

The same general procedure was used for all of the entries and is as follows: To a flask charged with amide (1.0 equiv) in $CH_2Cl_2$ (0.2 M), catalyst 3a (0.05 equiv in $CH_2Cl_2$) was added by cannulation followed by addition of styrene (1.9 equiv) via syringe. The flask was fitted with a condenser and refluxed under argon for 15 hours. The reaction is monitored by TLC analysis. After the solvent was evaporated, the product was purified directly on a silica gel column. The only deviation from this procedure is in Table 6, Entry 1b where 0.1 equivalents of catalyst 3a are used instead of 0.05 equivalents that is used in the rest of the reactions.

EXAMPLE 8
Representative Procedure for Reactions in Table 7:

To a flask charged with ethyl vinyl ketone (1.0 equiv) in $CH_2Cl_2$ (0.2M), catalyst 3a (0.05 equiv in $CH_2Cl_2$) was added by cannulation followed by addition of styrene (1.9 equiv) via syringe. The flask was fitted with a condenser and refluxed under argon for 15 hours. The reaction is monitored by TLC analysis. After the solvent was evaporated, the product was purified directly on a silica gel column to yield cross-metathesis product in quantitative yield and characterized exclusively as the trans isomer by $^1$H-NMR. The reactions described in Table 7 were conducted under the same reaction conditions with the equivalents of acrylates as listed in the table.

EXAMPLE 9
Representative Procedure for Reactions in Table 9:

The reaction conditions are analogous to those in Table 7. The ratios of styrene to terminal olefin are listed in Table 9.

EXAMPLE 10
Representative Procedure for Reactions in Table 10:

An analogous set of reaction conditions are employed for acrylate dimerization in entries 1–4. To a solution of 3a (5 mol %) in $CH_2Cl_2$ (0.4M) at room temperature was added the appropriate acrylate by syringe. The flask was fitted with a reflux condenser under a flow of nitrogen and the reaction mixture heated to 40° C. and was maintained at that temperature for 3 h. The black reaction mixture was cooled to room temperature and then was concentrated to 0.5 mL by rotary evaporation. The resulting residue was purified by silica gel chromatography (2×10 cm) to yield fumarate dimers as exclusive trans isomers by $^1$H-NMR.

For Table 10 Entries 5–7, the identical reaction conditions to those listed above apply, except that the substrate concentration was lowered to 0.05M in CH2C12 from 0.4M. Without being bound by theory, this change in reaction conditions is attributed to a more expedious bimolecular catalyst decomposition pathway of ketone carbenes versus ester carbenes.

EXAMPLE 11
Representative Procedure for Reactions in Table 11:

There are three sets of reaction conditions used in these reactions. For Table 11 Entries 1–2, a flask charged with catalyst 3a (0.05 equiv), α,β-unsaturated ketone (1 equiv) and α,β-unsaturated ester (2 equiv) were added via syringe. The flask was fitted with a condenser and refluxed under argon for 3 hours. TLC analysis is used to monitor the reaction. After the solvent was evaporated, the product was purified directly on a silica gel column. For Table 11 Entries 3–5, analogous reactions are used, except that the 1,1-disubstituted olefin is used in excess by 4 equivalents relative to the acrylate component. In addition, the products from these reactions were isolated as a 2 to 1 ratio of trans:cis diastereomers and were determined by $^1$H-NMR nOe determination. Finally, for Table 11 Entries 6–7, identical reaction conditions are used as for Entries 1–5 except that the methylenecyclohexane is added in a 2 equivalent excess relative to the acrylate cross-partner.

What is claimed is:

1. A method for preparing trisubstituted olefins comprising:
    contacting a geminal disubstituted olefin with a terminal olefin in the presence of a metal carbene metathesis catalyst of the formula $XX^1LL^1M=CRR^1$ to generate a tri-substituted olefin in an intermolecular olefin cross-metathesis reaction, wherein:
    M is ruthenium or osmium;
    L and $L^1$ are each, independently, any neutral electron donor;
    X and $X^1$ are each, independently, any anionic ligand; and
    R and $R^1$ are each independently selected from hydrogen or a substituent selected from the group consisting of $C_1$–$C_{20}$ alkyl, $C_2$–$C_{20}$ alkenyl, $C_2$–$C_{20}$ alkenyl, aryl, $C_1$–$C_{20}$ carboxylate, $C_1$–$C_{20}$ alkoxy, $C_2$–$C_{20}$, alkenyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, the substituent optionally substituted with one or more moieties selected from the group consisting of $C_1$–$C_{20}$ alkyl, $C_1$–$C_{20}$ alkoxy, aryl, and a functional group selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

2. The method of claim 1 wherein the catalyst is of the formula:

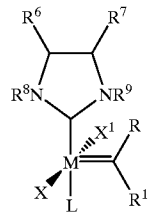

or

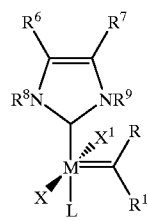

wherein:

M is ruthenium or osmium;

X and $X^1$ are each independently an anionic ligand;

L is a neutral electron donor ligand; and,

R, $R^1 R^6$, $R^7$, $R^8$, and $R^9$ are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, the substituent optionally substituted with one or more moieties selected from the group consisting of $C_1$–$C_{10}$ alkyl, $C_1$–$C_{10}$ alkoxy, aryl, and a functional group selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

3. The method of claim 2 wherein:

M is ruthenium;

L is selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether; and, X and $X^1$ are each independently hydrogen, halide, or a substituent selected from the group consisting of $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthiol, aryl thiol, $C_1$–$C_{20}$ alkylsulfonyl, and $C_1$ $C_{20}$ alkylsulfinyl, the substituent optionally substituted with one or more moieties selected from the group consisting of $C_1$–$C_{10}$ alkyl, $C_1$–$C_{10}$ alkoxy, aryl and halide.

4. The method of claim 3 wherein:

M is ruthenium;

X and $X^1$ are each independently selected from the group consisting of halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and trifluoromethanesulfonate;

L is a phosphine of the formula $PR^3R^4R^5$, where $R^3$, $R^4$, and $R^5$ are each independently aryl, $C_1$–$C_{10}$ alkyl, or cycloalkyl;

R is hydrogen; and, $R^1$ is phenyl or vinyl, optionally substituted with one or more moieties selected from the group consisting of $C_1$–$C_5$ alkyl, $C_1$–$C_5$ alkoxy, phenyl, and a functional group selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

5. The method of claim 4 wherein

X and $X^1$ are each chloride;

L is selected from the group consisting of -P(cyclohexyl)$_3$, -P(cyclopentyl)$_3$, -P(isopropyl)$_3$, and -P(phenyl)$_3$; and, $R^1$ is phenyl or —C=C(CH$_3$)$_2$.

6. The method of claim 5 wherein $R^6$ and $R^7$ together form a cycloalkyl or an aryl.

7. The method of claim 5 wherein $R^6$ and $R^7$ are the same and are hydrogen or phenyl.

8. The method of claim 5 wherein $R^8$ and $R^9$ are each independently a substituted or unsubstituted aryl.

9. The method of claim 5 wherein $R^8$ and $R^9$ are each independently of the formula

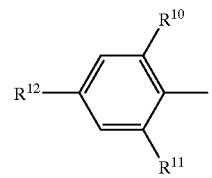

wherein $R^{10}$, $R^{11}$, and $R^{12}$ are each independently hydrogen, $C_1$–$C_{10}$ alkyl, $C_1$–$C_{10}$ alkoxy, aryl, or a functional group selected from hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

10. The method of claim 9 wherein $R^{10}$, $R^{11}$, and $R^{12}$ are each independently hydrogen, methyl or isopropyl.

11. The method of claim 1 wherein the terminal olefin is of the formula:

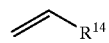

wherein $R^{14}$ is selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl; and wherein $R^{14}$ is substituted or unsubstituted.

12. The method of claim 11 wherein $R^{14}$ is substituted with one or more moieties selected from the group consisting of $C_1$–$C_{10}$ alkyl, $C_1$–$C_{10}$ alkoxy and aryl, wherein the moiety is substituted or unsubstituted.

13. The method of claim 12 wherein the moiety substitution is selected from the group consisting of halogen, a $C_1$–$C_5$ alkyl, $C_1$–$C_5$ alkoxy, and phenyl.

14. The method of claim 11 wherein $R^{14}$ contains one or more functional groups, wherein the functional group is selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

15. The method of claim 1 wherein the terminal olefin is of the formula:

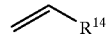

wherein $R^{14}$ is a functional group selected from the group consisting of thioether, ketone, aldehyde, ester, ether, amine, imine, amide, nitro, carboxylic acid, disulfide, carbonate, isocyanate, carbodiimide, carboalkoxy, carbamate, and halogen, wherein the functional group is substituted or unsubstituted.

16. The method of claim 1 wherein the geminal disubstituted olefin is of the formula

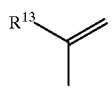

wherein $R^{13}$ is selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl; and wherein $R^{13}$ is substituted or unsubstituted.

17. The method of claim 11 wherein $R^{13}$ substituted with one or more moieties selected from the group consisting of $C_1$–$C_{10}$ alkyl, $C_1$–$C_{10}$ alkoxy and aryl, wherein the moiety is substituted or unsubstituted.

18. The method of claim 12 wherein the moiety substitution is selected from the group consisting of halogen, a $C_1$–$C_5$ alkyl, $C_1$–$C_5$ alkoxy, and phenyl.

19. The method of claim 16 wherein $R^{13}$ contains one or more functional groups, wherein the functional group is selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

20. The method of claim 1 wherein the geminal disubstituted olefin is of the formula

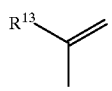

wherein $R^{13}$ is a functional group selected from the group consisting of thioether, ketone, aldehyde, ester, ether, amine, imine, amide, nitro, carboxylic acid, disulfide, carbonate, isocyanate, carbodiimide, carboalkoxy, carbamate, and halogen, wherein the functional group is substituted or unsubstituted.

21. The method of claim 1 wherein the disubstituted olefin is a substituted or unsubstituted α-functionalized olefin.

22. The method of claim 21 wherein the α-functionalized olefin is a substituted or unsubstituted acrylamide.

23. The method of claim 21 wherein the α-functionalized olefin is selected from the group consisting of a substituted or unsubstituted acrylate, vinyl ketone, and vinyl aldehyde.

24. The method of claim 1 wherein the trisubstituted olefin is prepared at room temperature.

25. A method for preparing di- or tri-substituted olefins comprising contacting a first substituted or unsubstituted electron deficient olefin with a second substituted or unsubstituted electron deficient olefin in the presence of a metal carbene metathesis catalyst of the formula $XX^1LL^1M=CRR^1$, wherein the first and second olefins are the same or different, to generate a di- or tri-substituted olefin in an intramolecular olefin cross-metathesis reaction; wherein M is ruthenium or osmium;

L and $L^1$ are each, independently, any neutral electron donor;

X and $X^1$ are each, independently, any anionic ligand; and

R and $R^1$ are each independently selected from hydrogen or a substituent selected from the group consisting of $C_1$–$C_{20}$ alkyl, $C_2$–$C_{20}$ alkenyl, $C_2$–$C_{20}$ alkenyl, aryl, $C_1$–$C_{20}$ carboxylate, $C_1$–$C_{20}$ alkoxy, $C_2$–$C_{20}$, alkenyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, the substituent optionally substituted with one or more moieties selected from the group consisting of $C_1$–$C_{20}$ alkyl, $C_1$–$C_{20}$ alkoxy, aryl, and a functional group selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

26. The method of claim 25 wherein the first olefin is a substituted or unsubstituted styrene and wherein the second olefin contains an α-carbonyl group.

27. The method of claim 26 wherein the second olefin is acrylate or acrylamide, and wherein the second olefin is substituted or unsubstituted.

28. The method of claim 25 wherein the first and second olefins each contain an α-carbonyl group.

29. The method of claim 25 wherein the first olefin is a substituted styrene and wherein the substitution occurs on one or more aromatic carbons.

30. The method of claim 25 wherein the first olefin is a substituted styrene and wherein the substitution occurs on the olefinic carbons.

31. The method of claim 25 wherein the first olefin is an ortho-substituted styrene.

32. The method of claim 25 wherein the first olefin is a terminal olefin and wherein the second olefin is an α-functionalized olefin.

33. A method for preparing di- or tri-substituted olefins comprising contacting a substituted or unsubstituted aliphatic olefin with a substituted or unsubstituted electron-deficient olefin in the presence of a metal carbene metathesis catalyst of the formula $XX^1LL^1M=CRR^1$ to generate a di- or tri-substituted olefin in an intermolecular olefin cross-metathesis reaction; wherein M is ruthenium or osmium;

L and $L^1$ are each, independently, any neutral electron donor;

X and $X^1$ are each, independently, any anionic ligand; and

R and $R^1$ are each independently selected from hydrogen or a substituent selected from the group consisting of $C_1$–$C_{20}$ alkyl, $C_2$–$C_{20}$ alkenyl, $C_2$–$C_{20}$ alkenyl, aryl, $C_1$–$C_{20}$ carboxylate, $C_1$–$C_{20}$ alkoxy, $C_2$–$C_{20}$, alkenyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, the substituent optionally substituted with one or more moieties selected from the group consisting of $C_1$–$C_{20}$ alkyl, $C_1$–$C_{20}$ alkoxy, aryl, and a functional group selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

34. The method of claim 33 wherein the metathesis catalyst is of the formula

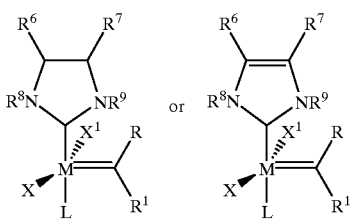

wherein:

M is ruthenium;

X and $X^1$ are each independently selected from the group consisting of halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and trifluoromethanesulfonate;

L is a phosphine of the formula $PR^3R^4R^5$, where $R^3$, $R^4$, and $R^5$ are each independently aryl, $C_1$–$C_{10}$ alkyl, or cycloalkyl;

R is hydrogen; and, $R^1 R^6$, $R^7$, $R^8$, and $R^9$ are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, the substituent optionally substituted with one or more moieties selected from the group consisting of $C_1$–$C_{10}$ alkyl, $C_1$–$C_{10}$ alkoxy, aryl, and a functional group selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

35. The method of claim 33 wherein the aliphatic olefin is a mono-, di- or trisubstituted olefin.

36. The method of claim 33 wherein the aliphatic olefin is substituted one or more groups selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl, wherein the substituent group is substituted or unsubstituted.

37. The method of claim 36 wherein the substituent group is substituted with one or more moieties selected from the group consisting of $C_1$–$C_{10}$ alkyl, $C_1$–$C_{10}$ alkoxy, and aryl, wherein the moiety is substituted or unsubstituted.

38. The method of claim 37 wherein the moiety is substituted with one or more groups selected from a halogen, a $C_1$–$C_5$ alkyl, $C_1$–$C_5$ alkoxy, and phenyl.

39. The method of claim 33 wherein the aliphatic olefin includes one or more functional groups selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

40. The method of claim 33 wherein the aliphatic olefin is 1-hexene and the electron-deficient olefin is methyl acrylate.

41. A method for preparing trisubstituted olefins comprising contacting a first substituted or unsubstituted styrene with a second substituted or unsubstituted α-functionalized olefin in the presence of a metathesis catalyst to form a cross-product and stilbene, and contacting the stilbene with unsubstituted α-functionalized olefin in the presence of a metathesis catalyst, wherein the catalyst is of the formula:

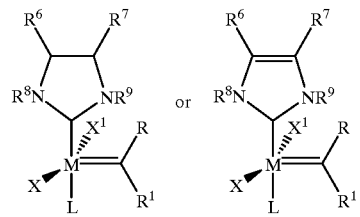

wherein:

M is ruthenium;

X and $X^1$ are each independently selected from the group consisting of halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and trifluoromethanesulfonate;

L is a phosphine of the formula $PR^3R^4R^5$, where $R^3$, $R^4$, and $R^5$ are each independently aryl, $C_1$–$C_{10}$ alkyl, or cycloalkyl;

R is hydrogen; and, $R^1 R^6$, $R^7$, $R^8$, and $R^9$ are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthiol, aryl thiol, $C_1$–$C_{20}$ alkylsulfonyl and $C_1$–$C_{20}$ alkylsulfinyl, the substituent optionally substituted with one or more moieties selected from the group consisting of $C_1$–$C_{10}$ alkyl, $C_1$–$C_{10}$ alkoxy, aryl, and a functional group selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

42. The method of claim 1 wherein at least one of L and $L^1$ is a substituted or unsubstituted N-heterocyclic carbene ligand.

43. The method of claim 25 wherein at least one of L and $L^1$ is a substituted or unsubstituted N-heterocyclic carbene ligand.

44. The method of claim 33 wherein at least one of L and $L^1$ is a substituted or unsubstituted N-heterocyclic carbene ligand.

* * * * *